United States Patent
Fuller et al.

(10) Patent No.: US 7,326,314 B2
(45) Date of Patent: Feb. 5, 2008

(54) METHOD OF MAKING A NONWOVEN ABSORBENT FABRIC

(75) Inventors: Charles Fuller, Kannapolis, NC (US);
John Steffen, Sugar Hill, GA (US);
Nyle Bishop, Mooresville, NC (US);
David Bye, Lawrenceville, GA (US)

(73) Assignee: Polymer Group, Inc., Charlotte, NC (US)

( * ) Notice: Subject to any disclaimer, the term of this patent is extended or adjusted under 35 U.S.C. 154(b) by 359 days.

(21) Appl. No.: 10/411,953

(22) Filed: Apr. 11, 2003

(65) Prior Publication Data

US 2003/0227106 A1 Dec. 11, 2003

Related U.S. Application Data

(60) Provisional application No. 60/372,243, filed on Apr. 12, 2002.

(51) Int. Cl.
*B29C 47/00* (2006.01)

(52) U.S. Cl. .................... 156/244.18; 156/252

(58) Field of Classification Search ............. 156/209, 156/219, 244.11, 244.24, 244.27, 244.18
See application file for complete search history.

(56) References Cited

U.S. PATENT DOCUMENTS

| | | | |
|---|---|---|---|
| 3,403,681 A * | 10/1968 | Hoey et al. ............. 604/383 |
| 3,459,618 A * | 8/1969 | Egler ..................... 156/219 |
| 3,989,867 A * | 11/1976 | Sisson .................... 428/132 |
| 4,033,341 A | 7/1977 | Scrivens |
| 4,184,498 A | 1/1980 | Franco |
| 4,381,326 A | 4/1983 | Kelly |
| 4,622,036 A | 11/1986 | Goodrum |
| 4,854,984 A * | 8/1989 | Ball et al. ............... 156/73.5 |
| 5,089,075 A * | 2/1992 | Sonoda .................. 156/244.18 |
| 5,370,764 A * | 12/1994 | Alikhan .................. 156/553 |
| 5,382,461 A | 1/1995 | Wu |
| 6,096,668 A | 8/2000 | Abuto et al. |
| 6,191,211 B1 | 2/2001 | Mussell et al. |
| 6,194,483 B1 * | 2/2001 | Tsai et al. ............... 523/105 |
| 6,264,864 B1 | 7/2001 | Mackay |
| 6,264,872 B1 | 7/2001 | Majors et al. |

FOREIGN PATENT DOCUMENTS

EP 0327328 A2 * 8/1989

* cited by examiner

*Primary Examiner*—Richard Crispino
*Assistant Examiner*—Barbara J. Musser
(74) *Attorney, Agent, or Firm*—Kilyk & Powersox, PLLC; Valerie Calloway

(57) ABSTRACT

The present invention is directed to a low-linting laminated nonwoven fabric comprised of a reticulated film layer and an associated absorbent layer, which is suitable for medical, hygiene, and industrial applications, wherein said nonwoven fabric performs to absorb liquids, such as human exudates, while significantly reducing the amount of particulates released. The reticulated film of the invention is comprised of a series or network of small, geometrically profiled, depressed areas, wherein the depressed areas of the film are able to collect liquids such as blood, and channel such liquids through openings in the film layer into the associated absorbent layer.

15 Claims, 3 Drawing Sheets

METHOD OF MAKING A NONWOVEN ABSORBENT FABRIC

TECHNICAL FIELD

The present invention relates generally to a laminated nonwoven fabric, and more specifically, to a low-linting laminated nonwoven fabric construct comprised of a reticulated film layer and an associated absorbent layer, such a construct exhibiting suitable performance for medical, industrial, and hygiene applications, wherein said nonwoven fabric performs to absorb liquids, such as human exudates or fluidic surface contaminants.

BACKGROUND OF THE INVENTION

Nonwoven fabrics are used in a wide variety of applications where the engineered qualities of the fabrics can be advantageously employed. The use of selected thermoplastic polymers in the construction of the fibrous fabric component, selected treatment of the fibrous component (either while in fibrous form or in an integrated structure), and selected use of various mechanisms by which the fibrous component is integrated into a useful fabric, are typical variables by which to adjust and alter the performance of the resultant nonwoven fabric.

Nonwoven fabric constructs comprising a polymeric film have proven to be particularly suitable for a variety of medical, hygiene, and industrial applications as such constructs permit cost-effective, disposable use. Use of such materials for surgical drapes, medical wipes, and the like has become increasingly widespread, since the physical properties and characteristics of the nonwoven fabric constructs can be selected as may be required for specific medical applications.

The utilization of a film-nonwoven construct in medical applications, such as surgical drapes, and hygiene applications, such as sanitary napkins, is known to those skilled in the art. The prior art to the aforementioned applications include U.S. Pat. No. 4,033,341 to Scrivens and U.S. Pat. No. 4,184,498 to Franco, which are both hereby incorporated by reference. Currently available absorbent constructs, comprising a net-like scrim layer over the absorbent layer, have proven to release unacceptable levels of the absorbent layer when employed in conditions of utmost contamination control. Further, such constructs have been found to be excessively noisy when the surface of the scrim layer comes into frictional contact with a surface.

Hygiene applications benefit from nonwoven fabric constructs comprised of a polymeric film, due to the level of comfort a nonwoven construct can provide when in intimate contact with the skin. Absorbent hygiene constructs, wherein nonwoven fabrics are utilized, tend to be multi-layered constructs consisting of at least one liquid permeable cover layer and one fluid acquisition layer that act to direct moisture away from the skin. Such constructs prove to be useful in: feminine care products, such as sanitary napkins and panty liners; diapers; and incontinence pads; and the like.

The reticulated film surface of the nonwoven fabric construct is comprised of a series of depressions that act to collect liquids and channel such into an associated underlying absorbent layer, while reducing potential release of particulates inherent to the absorbent layer. Further, the material of the present invention exhibits significantly reduced frictional noise and discomfort induced by prolonged contact.

SUMMARY OF THE INVENTION

The present invention is directed to a low-linting laminated nonwoven fabric comprised of a reticulated film layer and an associated absorbent layer, which is suitable for medical, hygiene, and industrial applications, wherein said nonwoven fabric performs to absorb liquids, such as human exudates, while significantly reducing the amount of particulates released. The reticulated film of the invention is comprised of a series or network of small, geometrically profiled, depressed areas, wherein the depressed areas of the film are able to collect liquids such as blood, and channel such liquids through openings in the film layer into the associated absorbent layer.

The reticulated film is typically comprised of an olefin polymer. The reticulated film of the invention is preferably produced by extruding a smooth, thin film of olefin polymer directly onto a construct forming apparatus, wherein any thermoplastic extrusion apparatus can be employed. The extruded film is formed directly into a reticulated sheet material without necessarily collecting the film as an intermediate product.

Optionally, the reticulated film may further comprise an aesthetic or performance-modifying surface modifying additive, wherein the modifying additive may be incorporated into the polymeric melt or topically applied. The use of such additives may include, but are not limited to, wetting agents, pigments, anti-microbials, emollients, fragrances, and the combination thereof.

The reticulated film may also optionally include thermoplastic rubbers, wherein the olefin polymer and the thermoplastic rubber are thoroughly combined into a homogeneous mixture. The addition of the thermoplastic rubber provides an elastomeric quality to the resultant reticulated film, allowing for a further improved level of conformability to the contact surface.

The absorbent layer of the present invention may be selected from any of various nonwoven constructs, such as a carded airlaid fabric, or a composite fabric comprised of natural fibers, synthetic fibers, as well as comprise particles of super absorbent material, or the combinations thereof. The absorbent layer of the construct may also optionally comprise an aesthetic or performance-modifying additive.

Also within the purview of the present invention is an alternate material, wherein the laminated nonwoven fabric construct may further comprise a liquid impermeable layer. In this embodiment, the absorbent layer is positioned medially to the reticulated film layer and the liquid impermeable backsheet layer. The liquid impermeable backsheet layer performs to protect the surrounding area from expression of the absorbed liquid that may occur from the absorbent layer.

The smooth, low-linting, laminate of the present invention is particularly suitable for medical applications, such as a surgical drape, wherein the laminate provides proper drainage of fluids through the network of small, geometrically profiled, depressed areas in the film. Further, the laminate is suitable for the topsheet of feminine hygiene products, such as sanitary napkins and panty liners, whereby the laminate acts to quickly direct bodily fluids away from the user, locking fluid within the underlying absorbent layer.

DETAILED DESCRIPTION OF THE INVENTION

Figure 1:
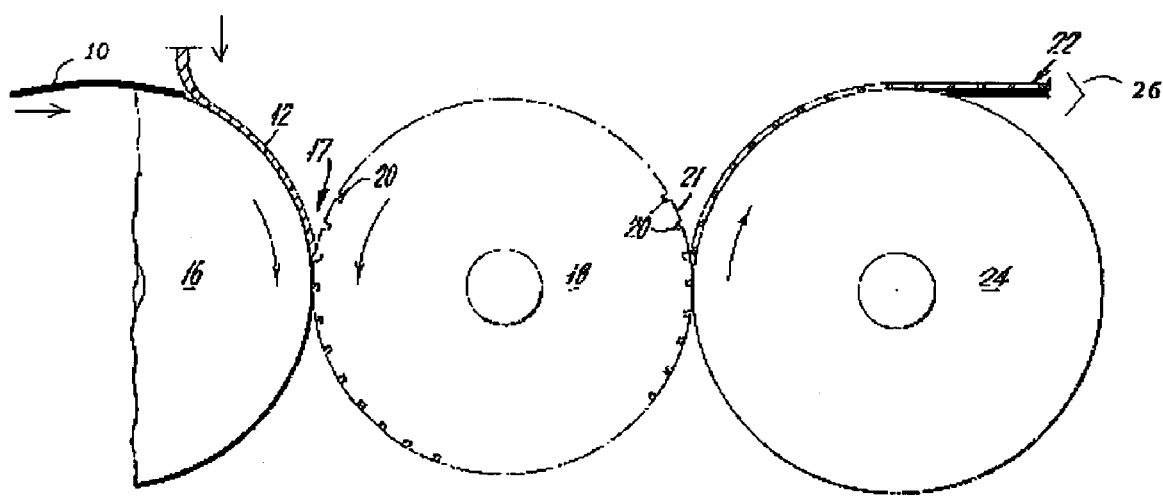
FIG. 1 is a schematic view in elevation of an arrangement of apparatus suitable for producing reticulated film layer/absorbent layer laminate material.
Figure 2:
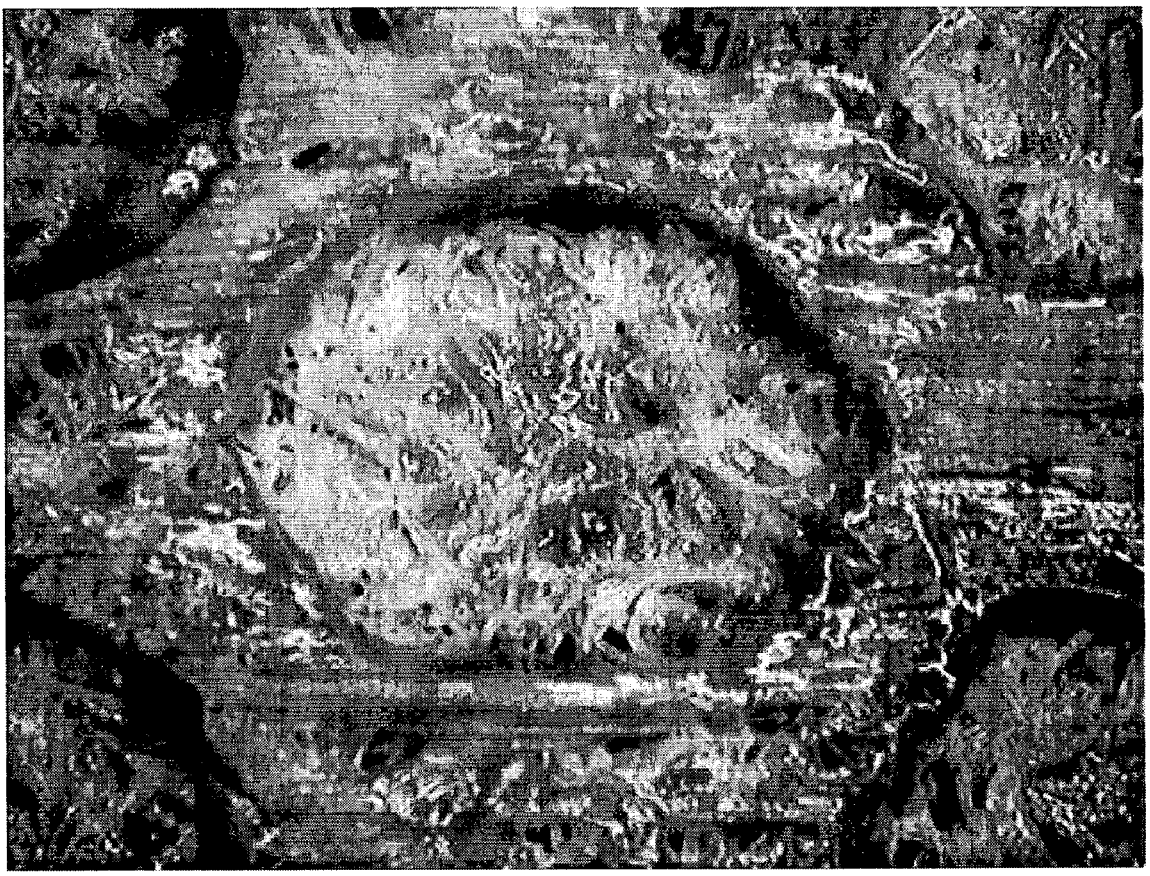
FIG. 2 is a photomicrograph of the top view of a laminate nonwoven fabric made in accordance with the present invention.
Figure 3:
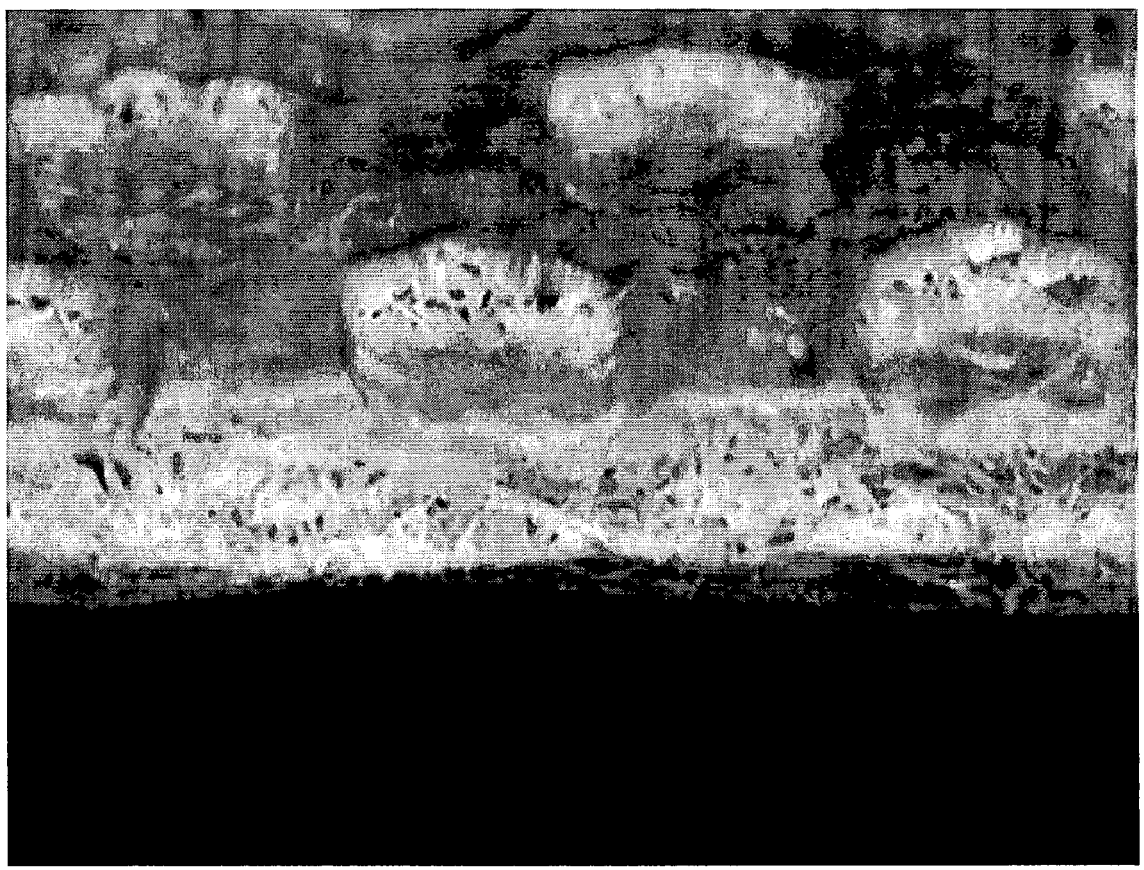
FIG. 3 is a photomicrograph of the side view of a laminate nonwoven fabric made in accordance with the present invention.

While the present invention is susceptible of embodiment in various forms, there is shown in the drawings, and will hereinafter be described, a presently preferred embodiment of the invention, with the understanding that the present disclosure is to be considered as an exemplification of the invention, and is not intended to limit the invention to the specific embodiment illustrated.

Within the purview of the present invention is a first embodiment, which comprises a reticulated film that is extruded directly onto an absorbent layer. The absorbent layer may be of various nonwoven fabric formations, including, but not limited to carded airlaid fabrics, hydroentangled fabrics, spunbond fabrics, or combinations thereof. Further, the absorbent layer may be comprised of super absorbent particles. The various aforementioned nonwoven formations may be comprised of various fibers, including natural fiber, such as wood pulp and viscose rayon, synthetic fibers, such as thermoplastic fiber including polyolefins, polyamides and polyesters, thermoset fibers, such as acrylics, and the combination thereof. The thermoplastic fibers may be further selected from homopolymers; copolymers, conjugates and other derivatives including those thermoplastic fibers having incorporated melt additives or surface-active agents.

In a second embodiment, the construct of the first embodiment may further include a liquid impermeable backsheet layer, wherein the absorbent layer is positioned medially to the reticulated film layer and the liquid impermeable layer. This embodiment protects the surrounding area from becoming contaminated with liquid that may be absorbed into the absorbent layer during use of the resultant product. The liquid impermeable layer may be selected from various thermoplastic compositions and blends, which impart either absolute, as represented by extruding a simple polyethylene layer, or selectively permeability, as by the use of monolithic or microporous films. Monolithic films, as taught in patent number U.S. Pat. No. 6,191,211, and microporous films, as taught in U.S. Pat. No. 6,264,864, both patents herein incorporated by reference, represent the mechanisms of forming such selectively permeable barrier films.

In accordance with the present invention, the nonwoven fabric is comprised of a reticulated film comprised of an olefin polymer, which is directly extruded onto an absorbent layer. The reticulated film, as described in U.S. Pat. No. 4,381,326 to Kelly, and hereby incorporated by reference, acts to effectively trap or entrain particulates inherent to the absorbent layer within the construct, preventing contamination of the surface with which the construct is in surface contact. The olefin polymers that are employed include, but are not limited to, isotactic polypropylene, linear low-density polyethylene, low-density polyethylene, high-density polyethylene, amorphous polypropylene, polybutylene, ethylene/vinyl acetate copolymer, ethylene/ethyl acrylate copolymer, ethylene/methyl acrylate copolymer, polystyrene, and the combination thereof.

The reticulated film may optionally comprise a mixture of olefin polymer and thermoplastic rubbers, wherein the preferred contemplated thermoplastic rubbers are known materials, and are exemplified as block copolymers having regions of polybutadiene or polyisoprene, and regions of polystyrene. A review article discussing these materials is "Structure And Properties of Block Polymers And Multiphase Polymer Systems: An Overview Of Present Status And Future Potential", by S. L. Aggarwal, Polymer, Vol. 17, November 1976, pages 938-956, hereby incorporated by reference. Two representative types of thermoplastic rubbers are the linear block copolymers (A-B-A) having a mid-block of polybutadiene or polyisoprene and end-blocks of polystyrene, and the "star" or "radial" block copolymers having from 4 to 20 "arms" connected to a common center. Each arm is an A-B block copolymer, the inner portion being polybutadiene or polyisoprene, with the outer portion being polystyrene.

Upon the inclusion of a thermoplastic rubber, the minimum amount of olefin polymer which can be employed in order to obtain an elastomeric quality is usually on the order of about 10 weight percent, based on weight of rubber to olefin polymer, although the proportion may be as low as about 5 weight percent (on the same basis) in some cases. The upper limit of olefin polymer will also vary from case to case, depending on the nature of the ingredients. At proportions above about 35 weight percent (on the same basis), a significant reduction in the characteristic recoverable elastomeric properties of the product begins to occur. Thus, the upper limit of olefin polymer would be that point at which the product still retains significant recoverable elastomeric characteristics.

Other additives can optionally be employed in the mixture. Such additives include pigments, anti-blocking agents, stabilizers, anti-oxidants, ultraviolet stabilizers, bonding aid, and the like.

Referring to the drawings, a mixture of thermoplastic rubber and olefin polymer is extruded in the form of a thin sheet 12 of molten material through a conventional slot die 14. The still molten sheet 12 is collected on a fibrous absorbent layer 10 and advanced onto a heated rotating roll 16 having a smooth surface. The heated smooth roll 16 has a predetermined peripheral speed. The temperature of the heated smooth roll 16 is such that the sheet 12 is molten and formable when the laminate product 26 reaches the nip 17 between the roll 16 and a second roll 18. The second (embossing) roll 18 is in contact with the smooth roll 16 at the said nip 17 between the two rolls. The embossing roll 18 has a resilient engraved surface. The engraving is in the form of continuous recessed areas 20 surrounding discontinuous raised areas 21. For instance, a preferred engraved pattern has a series of raised nubs (i.e., raised areas 21) running circumferentially around the surface of the embossing roll 18.

The laminate product 26 transfers from the smooth roll 16 to the embossing roll 18 at the nip 17 between the two rolls. The embossing roll 18 can be cooled upon the optional inclusion of a thermoplastic rubber, which solidifies while it is in contact therewith. The embossing roll 18 preferably is rotating at a slightly higher peripheral speed than the smooth roll 16. The speed differential is usually within the range of from 1 or 2 percent to about 15 to 20 percent greater, with about 3 to about 6 percent greater being more usual. The percentages are based upon the speed of the embossing roll. Similar speed differentials are employed when the embossing roll has a slightly lower peripheral linear speed than the heated roll. In some cases, the two rolls 16, 18 can rotate at the same speed, and in others, the embossing roll 18 can be slightly slower than the smooth roll 16. There is a wiping action at the nip 17, which forces substantially the entire molten sheet 12 into the recessed areas 20.

The surface of the heated smooth roll 16 is kept at a temperature such that the extruded sheet 12 is molten when it reaches the nip 17, as is evidenced by the sheet being able to form into a reticulated sheet upon contact with the embossing roll 18. Exact surface temperatures will vary from case-to-case, depending on the nature and temperature of the extruded sheet, the peripheral speed of the roll, and similar factors, but will usually be of the order of about 175 degree F. to about 350 degree F., and preferably about 200 degree F. to about 250 degree F.

The resultant laminate nonwoven fabric has a smooth surface, in addition to exhibiting a low-lint performance, making it particularly suitable for medical applications, as well as clean room applications, hygiene, and industrial end-use applications, including, but not limited to: surgical drapes and medical wipes; feminine hygiene products, such as sanitary napkins and panty liners; diapers and incontinence pads; absorbent wipes and spill control measures; and the like.

The laminate fabric of the present invention was tested for smoothness on a Kawabata Surface Tester—Model FB-4, as well as for linting in accordance with the Helmke Drum Test Method IEST-RP-CC003.2. The Kawabata Surface Test samples are cut 4"×10", placed over the tester in the machine direction, and clamped into place. The sensor is secured into position over the area to be tested. Adjust the balance screw on tester until Digital Volt Meter reads approximately 9.95 V. Further, the Sensor Micrometer is adjusted until the digital value reads 0.00 V (plus or minus 0.001). Actuating the start switch puts a drum in motion. Readings taken from the Kawabata Surface Tester are sent to a computer system and averaged. Table 1 reflects the results of the surface test, wherein the lower mV reading is indicative of a smoother surface. In addition, Table 1 also shows the Helmke Drum test results.

From the foregoing, it will be observed that numerous modifications and variations can be affected without departing from the true spirit and scope of the novel concept of the present invention. It is to be understood that no limitation with respect to the specific embodiments illustrated herein is intended or should be inferred. The disclosure is intended to cover, by the appended claims, all such modifications as fall within the scope of the claims.

TABLE 1

| | Helmke Drum Test | | | | | |
|---|---|---|---|---|---|---|
| Particles ≧0.5 um | Particles ≧0.7 um | Particles ≧1.0 um | Particles ≧2.0 um | Particles ≧3.0 um | Particles ≧5.0 um | Kawabata Smoothness Test Smoothness in mV |
| Sample A 12.3 | 9.62 | 6.77 | 3.27 | 1.67 | .0725 | 4 |

What is claimed is:

1. A method of making a low-lint laminated nonwoven fabric comprising the steps of:
   a. providing an olefin polymer;
   b. providing an absorbent layer, comprising a nonwoven fabric;
   c. providing a heated first roll having a smooth surface;
   d. providing an embossing second roll having an embossed surface comprising a series of raised nubs;
   e. extruding said olefin polymer into a continuous thin molten film directly onto said absorbent layer to form a laminate being advanced on said heated first roll wherein said heated first roll is rotating at a first peripheral speed;
   f. advancing said laminate with said thin molten film remaining molten and formable when said laminate reaches a nip between said heated first roll and said embossing second roll wherein said embossing second roll is rotating at a second peripheral speed that is from 1 to 20 percent different than said first peripheral speed of said heated first roll for embossing said film side of said laminate wherein said film side comes in contact with said embossing second roll, which is wiped with said raised nubs so as to reticulate said film side of said laminate to form a series or network of geometrically profiled depressed areas, wherein the difference in peripheral speeds of said heated first roll and said embossing second roll creates openings in the film layer in said depressed areas, and wherein the depressed areas of the film are able to collect liquids and channel said liquids through said openings in the film layer into the absorbent layer, to form a laminated fabric.

2. A method of making a laminated fabric as in claim 1, wherein said embossing second roll is rotating at said second peripheral speed that is from 1 to 20 percent greater than said first peripheral speed of said heated first roll.

3. A method of making a laminated fabric as in claim 1, wherein said heated first roll has a surface temperature of about 175° F. to about 350° F.

4. A method of making a laminated fabric as in claim 1, wherein said embossing second roll is cooled.

5. A method of making a laminated fabric as in claim 1, wherein said embossing second roll comprises a resilient engraved surface in the form of continuous recessed areas surrounding discontinuous raised areas.

6. A method of making a laminated fabric as in claim 1, further comprising providing said olefin polymer in a mixture with thermoplastic rubber.

7. A method of making a low-lint laminated nonwoven fabric comprising the steps of:
   a. providing an olefin polymer;
   b. providing an absorbent layer comprising a nonwoven fabric;
   c. providing a liquid impermeable backsheet;
   d. providing a heated first roll having a smooth surface;
   e. providing a an embossing second roll having an embossed surface comprising a series of raised nubs;
   f. extruding said olefin polymer into a continuous thin molten film directly onto said absorbent layer;
   g. positioning said liquid impermeable backsheet so that said absorbent layer is medial to said thin molten film and said backsheet to form a laminate being advanced on said heated first roll wherein said heated first roll is rotating at a first peripheral speed;
   h. advancing said laminate with said thin molten film remaining molten and formable when said laminate reaches a nip between said heated first roll and said embossing second roll wherein said embossing second roll is rotating at a second peripheral speed that is from 1 to 20 percent different than said first peripheral speed of said heated first for embossing said film side of said laminate wherein said film side comes in contact with said embossing second roll, which is wiped with said raised nubs so as to reticulate said film side of said laminate to form a series or network of geometrically profiled depressed areas, wherein the difference in peripheral speeds of said heated first roll and said embossing second roll creates openings in the film layer in said depressed areas, and wherein the depressed areas of the film are able to collect liquids and channel said liquids through said openings in the film layer into the absorbent layer, to form a laminated fabric.

8. A method of making a laminated fabric as in claim 7, wherein said olefin polymer is selected from the group consisting of isotactic polypropylene, polyethylene, linear low density polyethylene, low density polyethylene, high density polyethylene, amorphous polypropylene, polybutylene, ethylene/vinyl acetate copolymer, ethylene/ethyl acrylate copolymer, ethylene/methyl acrylate copolymer, polystyrene, and the combination thereof.

9. A method of making a laminated fabric as in claim 7, wherein said laminated fabric is a surgical drape.

10. A method of making a laminated fabric as in claim 7, wherein said laminated fabric is a feminine hygiene product component.

11. A method of making a laminated fabric as in claim 7, wherein said embossing second roll is rotating at said second peripheral speed that is from 1 to 20 percent greater than said first peripheral speed of said heated first roll.

12. A method of making a laminated fabric as in claim 7, wherein said heated first roll has a surface temperature of about 175° F. to about 350° F.

13. A method of making a laminated fabric as in claim 7, wherein said embossing second roll is cooled.

14. A method of making a laminated fabric as in claim 7, wherein said embossing second roll comprises a resilient engraved surface in the form of continuous recessed areas surrounding discontinuous raised areas.

15. A method of making a laminated fabric as in claim 7, further comprising providing said olefin polymer in a mixture with thermoplastic rubber.

* * * * *